US009815959B2

United States Patent
Lai et al.

(10) Patent No.: US 9,815,959 B2
(45) Date of Patent: Nov. 14, 2017

(54) METHOD FOR MANUFACTURING NOVEL HOLLOW PARTICLES

(71) Applicant: Gwo Xi Stem Cell Applied Technology Co., Ltd., Hsinchu County (TW)

(72) Inventors: Jui-Yang Lai, Hsinchu County (TW); Kao-Yuan Chang, Hsinchu County (TW); Zih-Han Hong, Hsinchu County (TW); Po-Cheng Lin, Hsinchu County (TW); Ming-Hsi Chuang, Hsinchu County (TW)

(73) Assignee: GWO XI STEM CELL APPLIED TECHNOLOGY CO., LTD., Zhubei, Hsinchu County (TW)

( * ) Notice: Subject to any disclaimer, the term of this patent is extended or adjusted under 35 U.S.C. 154(b) by 92 days.

(21) Appl. No.: 14/632,730

(22) Filed: Feb. 26, 2015

(65) Prior Publication Data
US 2015/0274923 A1 Oct. 1, 2015

Related U.S. Application Data

(60) Provisional application No. 61/945,364, filed on Feb. 27, 2014.

(51) Int. Cl.
| | |
|---|---|
| *C08J 9/36* | (2006.01) |
| *A61K 35/35* | (2015.01) |
| *A61L 27/22* | (2006.01) |
| *A61L 27/56* | (2006.01) |
| *A61L 27/58* | (2006.01) |
| *A61K 35/28* | (2015.01) |
| *A61K 9/50* | (2006.01) |
| *A61L 27/16* | (2006.01) |
| *A61L 27/18* | (2006.01) |
| *A61L 27/50* | (2006.01) |

(52) U.S. Cl.
CPC .............. *C08J 9/36* (2013.01); *A61K 9/5031* (2013.01); *A61K 35/28* (2013.01); *A61K 35/35* (2013.01); *A61L 27/16* (2013.01); *A61L 27/18* (2013.01); *A61L 27/22* (2013.01); *A61L 27/50* (2013.01); *A61L 27/56* (2013.01); *A61L 27/58* (2013.01); *A61L 2300/222* (2013.01); *A61L 2300/236* (2013.01); *A61L 2300/25* (2013.01); *A61L 2300/252* (2013.01); *A61L 2300/64* (2013.01); *A61L 2430/28* (2013.01); *C08J 2207/10* (2013.01); *C08J 2367/04* (2013.01); *C08J 2405/08* (2013.01)

(58) Field of Classification Search
CPC .... A61K 9/14; A61K 9/1647; A61K 51/1244; A61K 9/167; A61K 9/1694; A61K 2039/55555; A61K 9/16; A61K 9/1676; A61K 9/5057; A61K 9/5161; A61K 47/488; A61K 47/48884; A61K 47/48915; A61K 47/48923
USPC ........ 428/402–402.24, 403, 404, 407, 321.1, 428/474.4; 435/375, 307, 402; 427/331, 427/389.9, 212, 213–213.36, 483, 256; 424/725, 10.1, 76.2, 400, 408, 450, 451, 424/455, 93.7, 184.1, 497, 489, 501, 490, 424/491, 492, 493, 494, 495; 264/534, 5, 264/41, 4–4.7
See application file for complete search history.

(56) References Cited

U.S. PATENT DOCUMENTS

| | | | | |
|---|---|---|---|---|
| 8,268,264 | B2* | 9/2012 | Lenz | B03C 1/0332 422/500 |
| 2010/0184103 | A1* | 7/2010 | Jing | G01N 33/54393 435/7.32 |
| 2011/0123456 | A1* | 5/2011 | Pandit | A61K 9/5161 424/9.6 |

OTHER PUBLICATIONS

Yin et al., Journal of Colloid and Interface Science, 336 (2009) 155-161.*

* cited by examiner

*Primary Examiner* — Margaret Moore
(74) *Attorney, Agent, or Firm* — Muncy, Geissler, Olds & Lowe, P.C.

(57) ABSTRACT

A method for manufacturing a hollow particle is provided. The method comprises the steps of (a) providing a hollow particulate; (b) soaking the hollow particulate in an amine solution to form amine groups on the surface of the hollow particulate; (c) adding a polypeptide, and the polypeptide is linked to the amine groups on the surface of the hollow particulate; and (d) adding a target molecule, and the target molecule is bound to the amine group which are still not bound.

11 Claims, 4 Drawing Sheets

2a  2b  2c  2d

METHOD FOR MANUFACTURING NOVEL HOLLOW PARTICLES

CROSS-REFERENCE TO RELATED APPLICATIONS

This Non-provisional application claims priority under 35 U.S.C. §119(a) on Patent Application No(s). [61/945,364] filed in American United Sates Feb. 27, 2014, the entire contents of which are hereby incorporated by reference.

FIELD OF THE INVENTION

The present invention relates to a novel method for manufacturing novel hollow particles. More particularly, the invention relates to a novel method for manufacturing novel hollow particles link with a polypeptide and a target molecule.

BACKGROUND OF THE INVENTION

Technology related to fundamental and applied tissue engineering has been advanced for the purpose of developing transplantable artificial tissues as part of regenerative medicine. Specifically, studies including stem cell proliferation and differentiation, development of cytocompatible and biocompatible three-dimensional scaffolds, and construction of a variety of tissue engineering tools are now the most active research areas in regenerative medicine. Among them, scaffolds that are used to deliver stem cells or tissue cells therein are critical for the development of artificial tissues and organs Scaffold materials used for the regeneration of body tissues must act as a platform to which cells adhere to form three-dimensional tissues. They must also function as a temporary barrier between transplanted cells and host cells, and they must be nontoxic and biocompatible generating tolerable immune reactions, if any are to be generated. In addition, scaffold material must be biodegradable in vivo at a desired time when the transplanted cells have grown sufficiently to the point of being able to adequately function as a tissue.

Typically, scaffolds are prepared from synthetic or natural polymers or their composites, and are manufactured into three-dimensional structures which have a variety of morphologies and properties. Most commonly used synthetic biodegradable polymers include polyglycolic acid (PGA), polylactic acid (PLA), poly(lactic acid-co-glycolic acid) (PLGA), poly-ε-caprolactone (PCL), and derivatives and copolymers thereof, which can be used as biomaterials for scaffold preparation. Naturally biodegradable polymers as exemplified by collagen, alginate, hyaluronic acid, gelatin, chitosan, fibrin, etc., are also very useful candidates for this purpose. A variety of different forms of materials, such as sponges, gels, fibers, and microbeads, are applied for the fabrication of scaffolds, and the most popular ones are porous sponges and injectable hydrogels.

Wang, M., et al (Tissue Engineering, Volume 16, Number 5, 2010) discloses a porous PLGA scaffold used for inducing the differentiation of adipose-derived stem cells (ADSCs) with a hepatic inducing medium. PLGA particles cannot significantly improve the proliferation of ADSCs in a general medium. The results indicate that ADSCs are difficult to adhesively growth on PLGA scaffolds.

Kim S E, et al (Colloids and Surfaces B: Biointerfaces 122 (2014) 457-464) discloses a porous PLGA particles with heparin-dopamine (Hep) and lactoferrin (LF) for inducing the proliferation and differentiation of cells. According to the analysis results, the cell proliferation is not significant even if the particles are modified.

Accordingly, there are many technical barriers in achieving the goal of tissue engineering perfectly. For instances, the space for cell culture is not enough, yield is too low, the amount of carried cells is too low, and success rate of cell transplantation is too low. Therefore, a functional biomaterials system is needed to be used as a cell culture scaffold and transplant carrier.

SUMMARY OF THE INVENTION

The invention provides a method for manufacturing a hollow particle comprises: (1) providing a hollow particulate; (2) soaking the hollow particulate in an amine solution to form amine groups on the surface of the hollow particulate; (3) adding a polypeptide, and the polypeptide is linked to the amine groups on the surface of the hollow particulate; and (4) adding a target molecule, and the target molecule is bound to the amine group which are still not bound.

The amine solution of the step (2) include, but are not limited to the Hexamethylene diamine, glycine, adipic dihydrazide (ADH), PEG, NH2-PEG-NHS and NH2-PEG-NH2's DMSO solution.

In some embodiments, the polypeptide of the step (3) is pretreat with an active buffer to activing the carboxyl, and the active buffer includes MES buffers, EDC solution or NHS solution, furthermore, the pH value of the active buffer is between 5~6.

In some embodiments, the polypeptide of the step (3) is select from the group consist of the IKVAV, RGD, YIGSR, REDV, DGEA, VGVAPG, GRGDS, LDV, RGDV, PDSGR, RYWLPR, LGTIPG, LAG, RGDS, RGDF, HHLG-GALQAGDV, VTCG, SDGD, GREDVY, GRGDY, GRGDSP, VAPG, GGGGRGDSP, GGGGRGDY, FTLCFD, Poly-Lysine and MAX-1.

In some embodiments, the target molecule of the step (4) is select from the group consist of the Hyaluronic acid, Hyaluronic acid oxidation, Colleagen, Glucocorticoid, Galectin and osteopontin.

In some embodiments, the concentration of the target molecule of the step (4) is between 0.25~0.38%.

In some embodiments, the weight ratio of the target molecule and the hollow particulate of the step (4), is between 1:1.5 to 1:1.

The invention provides a method for manufacturing the hollow particulate is produced by following process, comprising: (a) providing a biodegradable material with emulsion formula; (b) providing a PVA solution and the concentration of the PVA solution is greater than 0.5% v/v; (c) the PVA solution processing a cooling step and a homogenizing step; (d) slowly drop the biodegradable material into the PVA solution and cause the emulsification and form the hollow particulate; and (e)lyophilizing the hollow particulate.

The biodegradable material include, but are not limited to the polylactic acid, poly(butylene succinate), poly(butylene succinate-co-butylene adipate), poly(butylene adipate-co-terephthalamide carboxylate), polyglycolic acid, poly(lactic acid-co-glycolic acid), polycaprolactone, polyvinyl alcohol, and the mixtures thereof.

In some embodiments, the PVA solution of the step (b) concentration is 1% v/v.

In some embodiments, the temperature of the cooling step is between 10~15° C.

In some embodiments, the speed of the homogenizing step is small than 1000 rpm.

The details of one or more embodiments of the invention are set forth in the description below. Other features or advantages of the present invention will be apparent from the following detailed description of an example and also from the appended claims.

DETAILED DESCRIPTION OF THE INVENTION

Figure 1:
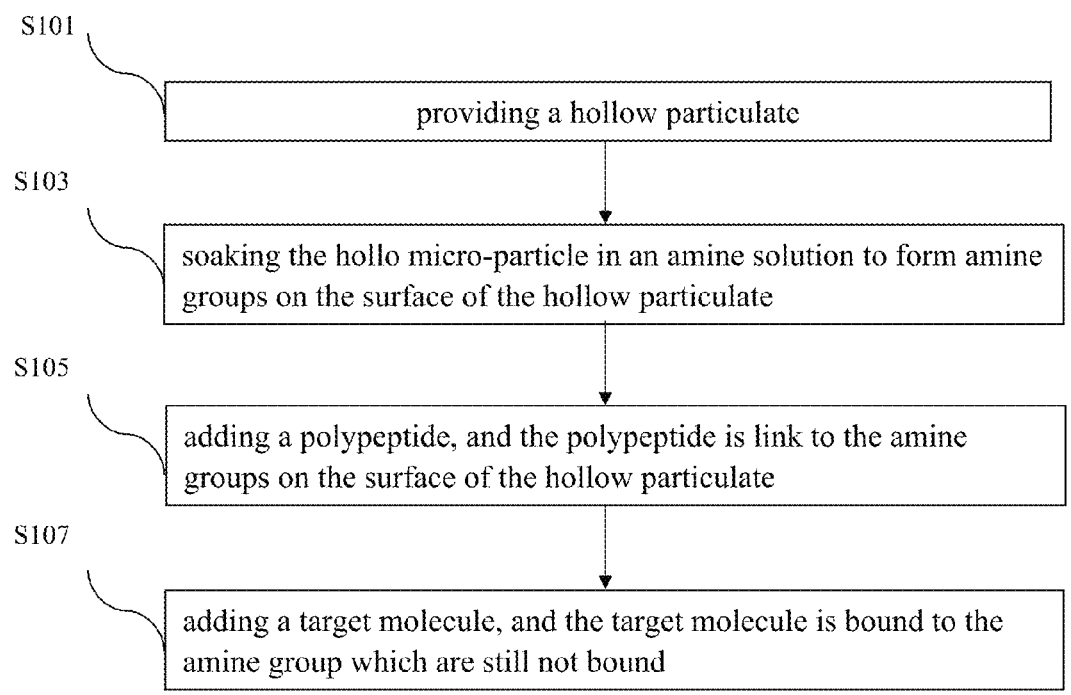
FIG. 1 illustrates a flowchart of the novel method for manufacturing novel hollow particles in this invention.
Figure 2:
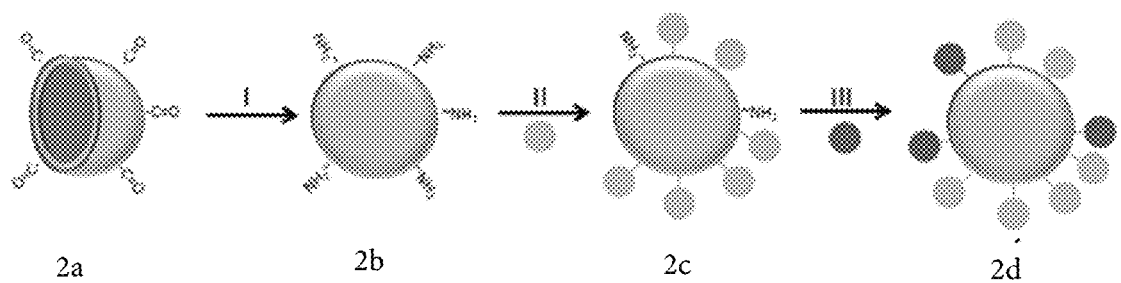
FIG. 2 illustrates a schematic diagram of the novel hollow particles in this invention.

The FIG. 1 and FIG. 2 illustrate the method for manufacturing a hollow particle. The embodiments and drawings provided here show different aspects of the present invention. However, the present invention is limited to neither the embodiments nor the drawings thereof.

The first invention is a method for manufacturing a hollow particle, the methods comprises the following steps: (1) providing a hollow particulate; (2) soaking the hollow particulate in an amine solution to form amine groups on the surface of the hollow particulate; (3) adding a polypeptide, and the polypeptide is link to the amine groups on the surface of the hollow particulate; and (4) adding a target molecule, and the target molecule is bound to the amine group which are still not bound.

According to the FIG. 1, the step S101, provide a hollow particle. This hollow particle is a kind of particulate, and the material, sharp and size is not limit. The material of the hollow particle (FIG. 2a) is biodegradable. The hollow particle can use for cell culture and cell deliver.

The material of the hollow particle include but not limit to the biostability polymer, fullerene, lipid or thereof. Biostability polymer means the biodegradable means the material polymer well not degrade in vivo. The biodegradable means the material well degrade in vivo. When the biodegradable material stay in the body fluids (blood), the material will be absorbed and/or removed gradually by human.

When the material of the hollow particle is biodegradable. The biodegradable material aliphatic polyester-aliphatic copolymer lipids, aliphatic, aromatic co-polyester lipids. Prefer biodegradable polymer is select from the group consist of the polylactic acid (PLA), poly(butylene succinate) (PBS), poly(butylene succinate-co-butylene adipate) (PBSA), poly(butylene adipate-co-terephthalamide carboxylate) (PBAT), polyglycolic acid (PGA), poly(lactic acid-co-glycolic acid) (PLGA), polycaprolactone (PCL), polyvinyl alcohol (PVOH), and the mixtures thereof.

In one embodiment, the PLGA hollow particle is product by two step emulsion process. The first emulsion process is put the PLGA into the $CH_2Cl_2$ solution and get the PLGA emulsion formula. Providing a PVA solution and the better concentration of the PVA solution is between 0.5% v/v ~1% v/v. Then cooling the PVA solution with the temperature of 10~15° C., the better temperature is 10° C. Stirring the PVA solution with the speed below the 1000 rpm, the better speed is between 500 rpm~1000 rpm. In order to decrease the pore size of the hollow particulate, the better manufacturing condition of the concentration of the PVA solution is between 0.5% v/v ~1% v/v and the PVA solution temperature is set between 10~20° C. While the stirring speed is set among 500 rpm, then hollow particle's pore size is among 120 μm. If the stirring speed is set to higher, then the pore size of the hollow particle will become to smaller.

In the second emulsion process, the PLGA slowly drop, by dropper, into the 1% v/v PVA solution with stirring speed of 500 rpm to form the emulsion formula PLGA particulate with sphere form and volatilize the $CH_2Cl_2$.

After that, remove the solution and wash the hollow PLGA particulate with RO water three times. Lyophilizing the hollow PLGA particulate for three days to get the solid hollow PLGA particulate. Then filter the solid hollow PLGA particulate to select 100~200 μm hollow PLGA particulate.

Soaking the hollow PLGA particulate into the amine solution (S103), to form amine groups on the surface of the hollow particulate. (FIG. 2b) The amine solution is select from the group consist of the Hexamethylene diamine, glycine, adipic dihydrazide (ADH), PEG, NH2-PEG-NHS and NH2-PEG-NH2's DMSO solution. The technical person could adjust the soak condition accord to the selected amine solution.

In one embodiment, soaking the hollow PLGA particulate (S101) in 10% 1,6-diamine isopropanol solution 3 hours to form amine groups ($NH_2$) on the surface of the hollow PLGA particulate (PLGA-$NH_2$). Centrifuging the solution to obtain the hollow PLGA-$NH_2$ particulate. Washing the hollow PLGA-$NH_2$ particulate with RO water three times. Lyophilizing the hollow PLGA-$NH_2$ particulate to get the solid hollow PLGA-$NH_2$ particulate.

The polypeptide is pretreat with an active buffer to activing the carboxyl. The active buffer includes but not limit to the MES buffers, EDC solution or NHS solution.

Adding the polypeptide to the hollow PLGA-$NH_2$ particulate, (S105) and the polypeptide is link to the amine groups ($NH_2$) on the surface of the hollow PLGA-$NH_2$ particulate. (FIG. 2c) The pH value of the reactive buffer is between 2~10. Prefer is pH 3~9 and the best is 4~8. The technical person could adjust the pH value accord to the selected reactive buffer. The concentration of the polypeptide is between 0.01 wt %~50 wt %. Prefer is between 1 wt %~40 wt % and best is between 10 wt %~30 wt %

The poly-peptide of this invention is means 2 or more than 2 poly-peptide or protein. The poly-peptide is a short-chain peptide, a oligo-peptide or a oligomer. Normally the length of the poly-peptide is between 2 to 20 amino acids, furthermore the better length of the poly-peptide is between 2 to 10 amino acids. The example of the poly-peptide in this invention is include but not limit to 2, 3, 4, 5, 6, 7, 8, 9 amino acids. In one embodiments, the poly-peptide include IKVAV, RGD, YIGSR, REDV, DGEA, VGVAPG, GRGDS, LDV, RGDV, PDSGR, RYWLPR, LGTIPG, LAG, RGDS, RGDF, HHLGGALQAGDV, VTCG, SDGD, GREDVY GRGDY, GRGDSP, VAPG, GGGGRGDSP, GGGGRGDY, FTLCFD, Poly-Lysine or MAX-1. The prefer embodiment is IKVAV.

In one embodiment (S103), shows the amine buffer prepare step. The MES buffer (PH 5.5) is made by add the concentration of the ratio of 1:1 of N, N-dimethylaminopropyl carbodiimide (EDC) to hydroxysuccinimide (NHS). Then add the PLGA-$NH_2$ particulate to the MES buffer to active the amine.

Then add the poly-peptide IKVAV into the MES buffer (S105). The concentration ratio of the IKVAV:EDC:NHS is among 5:5:1. After reactive for several times the PLGA-$NH_2$-IKVAV particulate is formed.

In one embodiment (S107), add the target molecule into the reactive MES buffer (S105) and the target molecule will link to the (PLGA-NH$_2$—) particulate which not cross-link to IKVAV. (FIG. 2d)

The target molecule can specific link to designed target unit, for example peptide, protein, nucleic acid polymers, aptamers or small molecule compound. The designed target unit is a tissue, cells, cellular structures (e.g., organelles), proteins, peptide, Polysaccharides or nucleic acid polymers. The aptamers of this invention means a random fragment molecule which selected by affinity level of the target unit. (Reference Cox and Ellington, Bioorg. Med. Chem. 9:2525-2531 (2001); Lee et al, Nuc. Acids Res. 32:D95-D100 (2004)). The aptamers are select but not limit DNA, RNA, peptide, protein, nucleic acid, small molecule compound. Micro-elements, inorganic compounds, cells and all organisms.

The target molecule is select from the group consist of the Hyaluronic acid, Hyaluronic acid oxidation, Colleagen, Glucocorticoid, Galectin and osteopontin.

In one embodiment, the target molecule is hyaluronic acid (HA). The hyaluronic acid can specific combine with liver cell. The target molecule can process amine reaction automatic. For example, the target molecule hyaluronic acid oxidation (oHA) cross-link to the hollow PLGA-NH$_2$ particulate through imine bond.

In one embodiment, dissolve the hyaluronic acid oxidation (oHA) in the water and add the alcohol slowly. Then add the PLGA-NH$_2$-IKVAV particulate (S105) into the hyaluronic acid oxidation (oHA) solution and sonicate the solution to form the hollow particles. The aldehyde group (—CHO) of the hyaluronic acid oxidation (oHA) can cross-link to the amine group (—NH) of the PLGA-NH$_2$-IKVAV to form the PLGA-NH$_2$-IKVAV-oHA hollow particles through the imine bond. Then wash the hollow particles with RO water twice, and soak the hollow particles in the alcohol. Furthermore, lyophilize the hollow particles to get the solid hollow particles.

The hollow particles of this invention comprise a 3D hollow structure. The hollow structure can culture and/or deliver the cell. The 3D hollow structure can mimic the body in vivo micro situation and provide the culture space. This 3D hollow structure particles can reduce the cell culture cost and increase the culture yield.

Furthermore, the hollow particles of this invention include a target molecule. The target molecule can take the hollow particles specific link to designed target unit, for example a tissue, cells, cellular structures (e.g., organelles), proteins, peptide, polysaccharides or nucleic acid polymers.

In summary, the hollow particles of this invention have more cell culture capacity than the traditional deliver. More particularly, the designed target molecule of the hollow particles can bring the hollow particles specific target link to the target unit. This technical can be powerful use in the cell therapy.

Figure 3A:
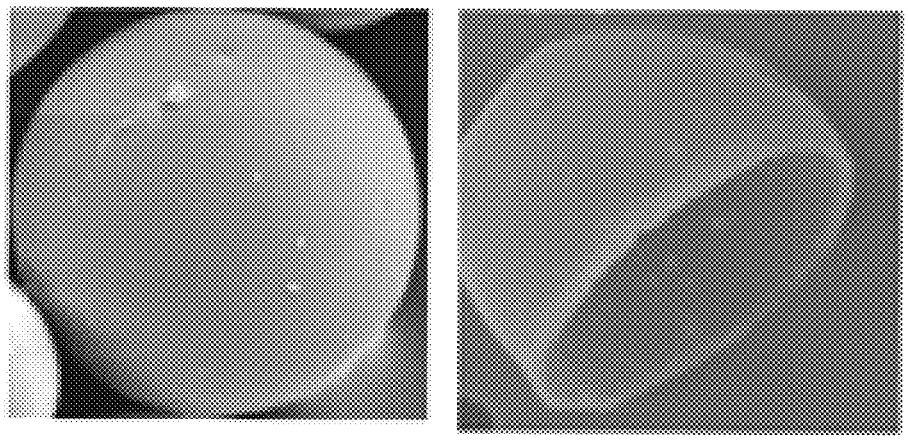
FIG. 3a-3e shows the PLGA particulate, PLGA-NH2 particulate, PLGA-NH2-IKVAV, PLGA-NH2-IKVAV-oHA, the outside and inside view of the solid PLGA-IKVAV particulate.

Embodiment 1
1.1 Manufacture of the Hollow Particles (Example 1)
PLGA Particulate Manufacture Process The PLGA particulate were manufactured by double emulsion method. Briefly, 0.9 g of PLGA dissolved in 40 ml of methylene chloride (2.25%) was mixed with 20 ml of ddH$_2$O, and then homogeneous mixed to conduct the first emulsification. 2.5 g of PVA and 250 ml of ddH$_2$O were mixed to prepare 1% PVA solution. 1% PVA solution was cooled to 10° C., then mixed at 500 rpm. The product of the first emulsification was slowly dropped in the stirred 1% PVA solution by a dropper. After removal of the solution, the product was washed three times with ddH$_2$O, and free-dried for three days to obtain PLGA particulate. The PLGA particulate were screened through screen mesh to obtain the PLGA particulate with a diameter of 100 to 200 μm. Referring to FIG. 3a, the scanning electron microscope (SEM) observation indicates that PLGA particulate inside had porous structures.

1.2 Formation of Amino Groups on PLGA Particulate

Figure 3B:
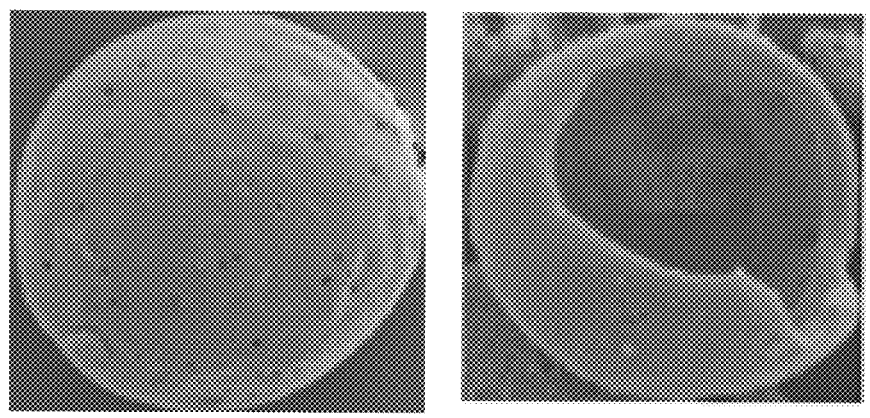

PLGA particulate were soaked in 10% 1,6-hexanediamine/isopropanol solutions for 3 hours, and then centrifuged to obtain PLGA-NH$_2$ particulate. The supernatant was retained for Nihydrin assay described in Example 2 to detect the linkage of amino groups. The particulate were washed three times with ddH$_2$O. Amino groups were formed on the surface of PLGA particulate to become PLGA-NH$_2$ particulate. Referring to FIG. 3b, the surface of PLGA-NH$_2$ was rough.

Figure 3C:
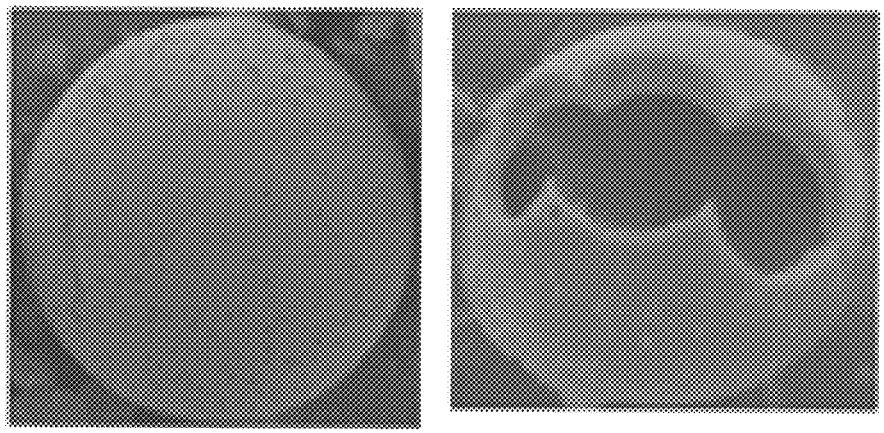

1.3 Grafting of PLGA-IKVAV 0.1 M of MES buffer solution (pH 5.5) was prepared. N,N-dimethylaminopropyl carbodiimide (EDC) and hydroxysuccinimide (NHS) were added in a ration of 1:1, and then IKVAV polypeptide was added to activate carboxyl groups for two hours. The ration of IKVAV: EDC: NHS was 5:5:1. The PLGA-NH$_2$ was added for the grafting reaction to occur. The concentration of IKVAV was 14 wt % in the solution. After 24 hours, the PLGA-NH2-IKVAV particulate were formed. The supernatant was retained for TNBS assay described in Example 3 to detect the Grafting of IKAVA. Referring to FIG. 3c, IKVAV was covered on the surface of PLGA-NH$_2$, and the surface of PLGA-NH$_2$ was smooth.

1.4 Grafting of PLGA-oHA

Figure 3D:
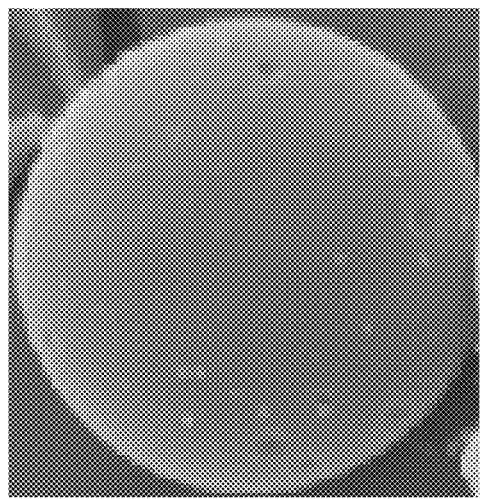
Figure 3D:
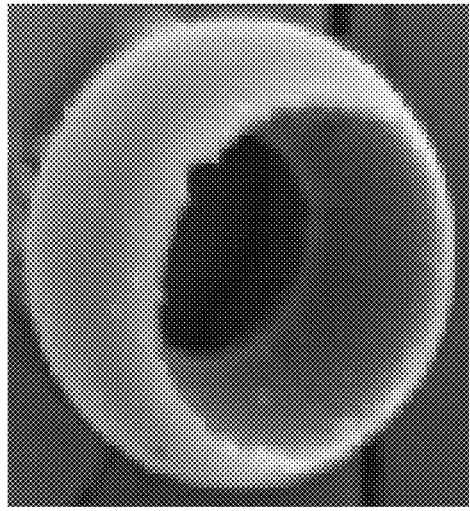
Figure 3E:
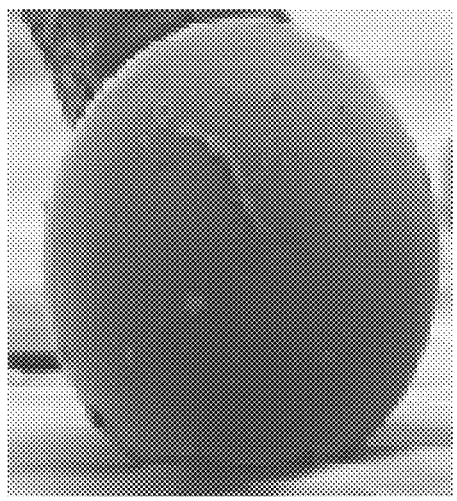
Figure 3E:
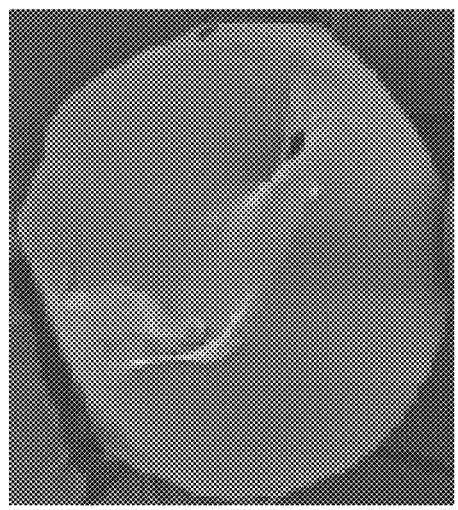

Finally, 150 mg of hyaluronic acid (oHA) dissolved in ddH$_2$O was slowly mixed with 99.5% of ethanol. 150 mg of PLGA-NH$_2$-IKVAV particulate were added and then mixed at 150 rpm for 24 hours at pH11. The supernatant was retained for TNBS assay to detect the grafting of oHA. The particulate were washed two times with ddH$_2$O, soaked in 30% and 95% ethanol for 10 minutes, respectively, and then freeze-dried. Because the aldehyde groups of oHA were reacted with the amine groups of the particulate to form imine bonds, PLGA-NH$_2$-IKVAV-oHA particles were produced, as shown in FIG. 3d.

Embodiment 2
Manufacture of the Hollow Particles (Test 1)
PLGA Particle Manufacture Process (Test 1)

The concentration of the compared PVA solution is 0.5%, The speed of the homogenizer increased to 1000 rpm, and the second emulsification is process without drop. The result is compare with the example 1.

TABLE 1

Compare the test 1 with the example 1

| | Condition | Result |
|---|---|---|
| Example 1 | 1% PVA solution | Surface porous size of PLGA particulate is smaller |
| Test 1 | 0.5% PVA solution | Surface porous size of PLGA particulate is bigger |
| Example 1 | PVA solution in low temperature | Surface porous size of PLGA particulate is smaller |
| Test 1 | PVA solution in room temperature | Surface porous size of PLGA particulate is bigger |
| Example 1 | Homogenizer speed is 500 rpm | Size of the PLGA particulate is among 120 μm |
| Test 1 | Homogenizer speed is 1000 rpm | Size of the PLGA particulate is <100 μm |
| Example 1 | Drop the PLGA emulsion | Form sphere product easily |

TABLE 1-continued

Compare the test 1 with the example 1

| | Condition | Result |
|---|---|---|
| | formula slowly into PVA solution | |
| Test 1 | Emulsification directly | Form sphere product hardly |

PLGA Particle Manufacture Process (Test 2)
PLGA-oHA

The condition of the test 2 PLGA particle is different from the example 1. The oxide-HA concentration is 300 mg, and PLGA-NH2-IKVAV particulate is 300 mg, and the sonication speed is set to 180 rpm. (Table 2)

TABLE 2

Compare of the test 2 with the example 1

| | Condition | Result |
|---|---|---|
| Example 1 | oHA 150 mg | cross-link hardly |
| Test 2 | oHA 300 mg | cross-link easily |
| Example 1 | PLGA-NH2-IKVAV particulate 150 mg | cross-link hardly |
| Test 2 | PLGA-NH2-IKVAV particulate 300 mg | cross-link easily |
| Example 1 | sonication speed 150 rpm | cross-link hardly |
| Test 2 | sonication speed 180 rpm | cross-link easily |

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following.

What is claimed is:

1. A method for manufacturing a hollow particle comprises:
    (1) providing a hollow particulate;
    (2) soaking the hollow particulate in an amine solution to form amine groups on the surface of the hollow particulate;
    (3) adding a polypeptide, and the polypeptide is linked to the amine groups on the surface of the hollow particulate; and
    (4) adding a target molecule, and the target molecule is bound to the amine group which is still not bound to the polypeptide;
    wherein the hollow particulate is formed by homogenizing the hollow particulate at a speed;
    wherein the speed is lower than 1000 rpm;
    wherein the concentration of the target molecule of the step (4) is between 0.25~0.38 wt %.

2. The method according to claim 1, wherein the step (1) of the hollow particulate comprises:
    (a) providing a biodegradable material, wherein the biodegradable material dissolved in methylene chloride solution is mixed with ddH$_2$O, and then homogeneous mixed to conduct the first emulsification;
    (b) providing a PVA solution and the concentration of the PVA solution is greater than 0.5% v/v;
    (c) cooling the PVA solution with the temperature of 10~15° C., then stirring the PVA solution with the speed below the 1000 rpm;
    (d) dropping slowly of the biodegradable material into the PVA solution and causing the second emulsification and forming the hollow particulate; and
    (e) lyophilizing the hollow particulate.

3. The method according to claim 2, wherein the biodegradable material is select from the group consist of the polylactic acid, poly(butylene succinate), poly(butylene succinate-co-butylene adipate), poly(butylene adipate-co-terephthalamide carboxylate), polyglycolic acid, poly(lactic acid-co-glycolic acid), polycaprolactone, polyvinyl alcohol, and the mixtures thereof.

4. The method according of claim 2, wherein the PVA solution of the step (b) concentration is 1% v/v.

5. The method according of claim 1, wherein the amine solution of the step (2) is selected from the group consisting of the Hexamethylene diamine, glycine, adipicdihydrazide (ADH), PEG amination solution, NH2-PEG-NHS and NH2-PEG-NH2's DMSO solution.

6. The method according of claim 1, wherein the polypeptide of the step (3) is pretreated with an active buffer to activate a carboxyl group.

7. The method according of claim 6, wherein the active buffer includes MES buffers, EDC solution or NHS solution.

8. The method according of claim 6, wherein the pH value of the active buffer is between 5~6.

9. The method according of claim 1, wherein the polypeptide of the step (3) is select from the group consist of the IKVAV, RGD, YIGSR, REDV, DGEA, VGVAPG, GRGDS, LDV, RGDV, PDSGR, RYWLPR, LGTIPG, LAG, RGDS, RGDF, HHLGGALQAGDV, VTCG, SDGD, GREDVY, GRGDY, GRGDSP, VAPG, GGGGRGDSP, GGGGRGDY, FTLCFD, Poly-Lysine and MAX-1;
    wherein A means (Alanine), F means (Phenylalanine), C means (Cysteine), U means (Selenocysteine), D means (Aspartic acid/Aspartate), N means (Asparagine), E means (Glutamic acid/Glutamate), Q means (Glutamine), G means (Glycine), H means (Histidine), L means (Leucine), I means (Isoleucine), K means (Lysine), O means (Pyrrolysine), M means (Methionine), P means (Proline), R means (Arginine), S means (Serine), T means (Threonine), V means (Valine), W means (Tryptophan), and Y means (Tyrosine).

10. The method according of claim 1, wherein the target molecule of the step (4) is selected from the group consisting of the Hyaluronic acid, Hyaluronic acid oxidation, Colleagen, Glucocorticoid, Galectin and osteopontin.

11. The method according of claim 1, wherein in the step (4), the weight ratio of the target molecule and the hollow particulate is between 1:1.5 to 1:1.

* * * * *